United States Patent
Espy et al.

(10) Patent No.: US 9,254,097 B2
(45) Date of Patent: Feb. 9, 2016

(54) SYSTEM AND METHOD FOR MAGNETIC CURRENT DENSITY IMAGING AT ULTRA LOW MAGNETIC FIELDS

(71) Applicant: LOS ALAMOS NATIONAL SECURITY, LLC, Los Alamos, NM (US)

(72) Inventors: Michelle A. Espy, Los Alamos, NM (US); John Stevens George, White Rock, NM (US); Robert Henry Kraus, White Rock, NM (US); Per Magnelind, Los Alamos, NM (US); Andrei Nikolaevich Matlashov, Los Alamos, NM (US); Don Tucker, Eugene, OR (US); Sergei Turovets, Eugene, OR (US); Petr Lvovich Volegov, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 70 days.

(21) Appl. No.: 13/622,940

(22) Filed: Sep. 19, 2012

(65) Prior Publication Data

US 2013/0072780 A1    Mar. 21, 2013

Related U.S. Application Data

(60) Provisional application No. 61/536,482, filed on Sep. 19, 2011, provisional application No. 61/674,129, filed on Jul. 20, 2012.

(51) Int. Cl.
*A61B 5/05* (2006.01)
*A61B 5/0476* (2006.01)

(Continued)

(52) U.S. Cl.
CPC .............. *A61B 5/05* (2013.01); *A61B 5/0035* (2013.01); *A61B 5/0476* (2013.01); *A61B 5/055* (2013.01);

(Continued)

(58) Field of Classification Search
None
See application file for complete search history.

(56) References Cited

U.S. PATENT DOCUMENTS

| 4,390,840 A | 6/1983 | Ganssen |
| 5,804,967 A | 9/1998 | Miller |

(Continued)

FOREIGN PATENT DOCUMENTS

| WO | WO 2008/008447 | | 1/2008 |
| WO | WO 2012070738 | * | 5/2012 |

OTHER PUBLICATIONS

Machine translation of Korean Patent Application No. 10-2010-0116596 (published on May 31, 2012), used as an English language equivalent of WO 2012070738.*

(Continued)

*Primary Examiner* — Long V Le
*Assistant Examiner* — Kevin Pontius

(57) ABSTRACT

Preferred systems can include an electrical impedance tomography apparatus electrically connectable to an object; an ultra low field magnetic resonance imaging apparatus including a plurality of field directions and disposable about the object; a controller connected to the ultra low field magnetic resonance imaging apparatus and configured to implement a sequencing of one or more ultra low magnetic fields substantially along one or more of the plurality of field directions; and a display connected to the controller, and wherein the controller is further configured to reconstruct a displayable image of an electrical current density in the object. Preferred methods, apparatuses, and computer program products are also disclosed.

13 Claims, 4 Drawing Sheets

(51) Int. Cl.

| | | |
|---|---|---|
| *G01R 33/32* | (2006.01) | |
| *G01R 33/54* | (2006.01) | |
| *G01R 33/44* | (2006.01) | |
| *G01R 33/48* | (2006.01) | |
| *A61B 5/053* | (2006.01) | |
| *A61B 5/055* | (2006.01) | |
| *A61B 5/00* | (2006.01) | |

(52) U.S. Cl.
CPC .............. *A61B 5/0536* (2013.01); *G01R 33/32* (2013.01); *G01R 33/445* (2013.01); *G01R 33/4808* (2013.01); *G01R 33/54* (2013.01); *G01R 33/326* (2013.01)

(56) References Cited

U.S. PATENT DOCUMENTS

| | | | |
|---|---|---|---|
| 5,919,142 A * | 7/1999 | Boone et al. | 600/547 |
| 6,397,095 B1 * | 5/2002 | Eyuboglu et al. | 600/411 |
| 6,577,125 B2 | 6/2003 | Prammer | |
| 6,674,282 B2 | 1/2004 | Pines | |
| 7,059,524 B2 | 6/2006 | Knowles | |
| 7,061,237 B2 | 6/2006 | Pines | |
| 7,187,169 B2 | 3/2007 | Clarke | |
| 7,251,310 B2 | 7/2007 | Smith | |
| 7,394,250 B2 | 7/2008 | Itozaki | |
| 7,397,241 B2 | 7/2008 | Gauthausen | |
| 7,541,806 B2 | 6/2009 | Appelt | |
| 7,573,268 B2 | 8/2009 | Volegov et al. | |
| 7,603,158 B2 * | 10/2009 | Nachman et al. | 600/411 |
| 7,688,069 B2 | 3/2010 | Kraus, Jr. | |
| 7,729,740 B2 | 6/2010 | Kraus, Jr. et al. | |
| 2005/0270026 A1 | 12/2005 | Guthausen | |
| 2006/0273786 A1 | 12/2006 | Smith | |
| 2007/0063700 A1 | 3/2007 | Levitt | |
| 2008/0074113 A1 | 3/2008 | Clarke | |
| 2008/0284433 A1 | 11/2008 | Kraus, Jr. et al. | |
| 2009/0102480 A1 * | 4/2009 | Katscher et al. | 324/309 |
| 2009/0289629 A1 | 11/2009 | Tuchman | |
| 2010/0090697 A1 | 4/2010 | Savukov et al. | |
| 2010/0219827 A1 | 9/2010 | Matlashov et al. | |

OTHER PUBLICATIONS

Bodurka, et al., Toward Direct Mapping of Neuronal Activity: MRI Detection of Ultraweak, Transient Magnetic Field Changes; 47 Magnetic Resonance in Medicine, pp. 1052-1058 (2002).

Espy, et al., SQUID-Based Simultaneous Detection of NMR and Biomagnetic Signals at Ultra-Low Magnetic Fields; IEEE Transactions on Applied Superconductivity, vol. 15, No. 2, Jun. 2005, pp. 635-639.

Espy, et al., Ultra-low Field MRI for the Detection of Liquid Explosives Using SQUIDs; IEEE/CSC & ESAS European Superconductivity News Forum, No. 9, Apr. 2009, pp. 1-12.

Matlachov, et al., SQUID detected NMR in microtesla magnetic fields; Journal of Magnetic Resonance, 170 (2004) pp. 1-7.

McDermott, et al., Liquid-State NMR and Scalar Couplings in Microtesla Magnetic Fields; Science Mar. 22, 2002, pp. 2247-2249.

Xiong, et al., Directly Mapping Magnetic Field Effects of Neuronal Activity by Magnetic Resonance Imaging; Human Brain Mapping, vol. 20, pp. 41-49 (2003).

* cited by examiner

Substitute Sheet

SYSTEM AND METHOD FOR MAGNETIC CURRENT DENSITY IMAGING AT ULTRA LOW MAGNETIC FIELDS

CLAIM OF PRIORITY

The present application claims priority to U.S. Provisional Patent Application Ser. No. 61/536,482 filed on 19 Sep. 2011 and entitled "Magnetic Resonance Current Density Imaging and Electrical Impedance Tomography at Ultra-low Magnetic Fields," and to U.S. Provisional Patent Application Ser. No. 61/674,129 filed on 20 Jul. 2012 and entitled "Ultra-low Field Functional Magnetic Resonance Combined with Magnetoencephalography," the entirety of both of which are incorporated herein by this reference.

STATEMENT REGARDING FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

TECHNICAL FIELD

The invention generally relates to the field of medical imaging, and more particularly to the field of magnetic resonance imaging at ultra low magnetic fields.

BACKGROUND AND SUMMARY

Various imaging techniques have been developed for the investigation of biological and other specimens. Some of these techniques (for example, magnetic resonance imaging and positron emission tomography) have become routine in clinical applications. Most imaging techniques rely on particular specimen properties to produce image contrast. For example, magnetic resonance images can depend on specimen spin $T_1$ or $T_2$ relaxation times, or spin densities. Magnetic resonance imaging has also been applied to so-called functional imaging (functional MRI or fMRI) so that magnetic resonance images can be associated with specimen brain function related to blood flow or oxygenation and not merely with specimen structure. Unfortunately, most magnetic resonance imaging systems require application of very high magnetic fields (1 Tesla or more), and thus require expensive, complex magnets. In addition, these high magnetic fields are problematic for clinical measurements of other types, due to the undesirable effects of large magnetic fields on other instrumentation that might be necessary for specimen measurements. In addition, while such magnetic resonance imaging methods generally have spatial resolution on the scale of millimeters (mm), they have poor temporal resolution, typically, no better than a few seconds. However, imaging methods in clinical and other applications can typically be selected to provide high spatial resolution images that lack high temporal resolution dynamic functional information, or to provide high temporal resolution functional information that cannot be readily associated with any specimen features or locations. Unfortunately, the use of magnetic resonance imaging in combination with other clinical measurement techniques is generally challenging, and improved methods and apparatus are needed.

Accordingly, aspects of the present invention can include a preferred system including an electrical impedance tomography apparatus electrically connectable to an object; an ultra low field magnetic resonance imaging apparatus including a plurality of field directions and disposable about the object; a controller connected to the ultra low field magnetic resonance imaging apparatus and configured to implement a sequencing of one or more ultra low magnetic fields substantially along one or more of the plurality of field directions; and a display connected to the controller. The controller can be further configured to reconstruct a displayable image of an electrical current density in the object. Additional aspects of the present invention can include a preferred method that includes delivering an electrical current through an object in a predetermined current direction; pulsing an ultra low magnetic field along one or more field directions; changing the direction of the ultra low magnetic field to another of the one or more field directions; detecting a resonance between the magnetic field associated with the applied electrical current and the nuclear spins within the ultra low magnetic field inside the object; and reconstructing an image of an electrical current density in the object in response to the detected resonance. In additional aspects of the present invention, the preferred system and method can be implemented at least in part in a distributed computing system and/or computer program product. These and other aspects, advantages, and salient features of the preferred embodiments of the present invention are described in detail below with reference to the following Figures.

DETAILED DESCRIPTION OF THE PREFERRED EMBODIMENTS

The following description of the preferred embodiments of the present invention and variations thereof is made with reference to the Figures and one or more illustrative example configurations and/or implementations. Those of skill in the art will recognize that the following description is for illustrative purposes only, and that the scope of the present invention is defined exclusively by the following claims.

Preferred System

Figure 1:
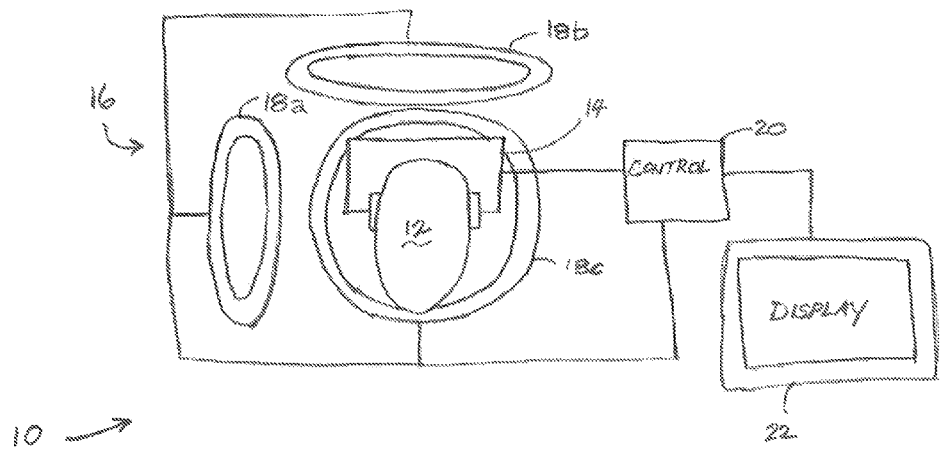
FIG. 1 is a schematic block diagram of a system for magnetic resonance imaging at ultra low magnetic fields in accordance with a preferred embodiment of the present invention.

As shown in FIG. 1, a preferred system 10 can include an electrical impedance tomography apparatus 14 electrically connectable to an object 12; an ultra low field magnetic resonance imaging apparatus 16 including a plurality of field directions and disposable about the object 12; a controller 20 connected to the ultra low field magnetic resonance imaging apparatus 16 and configured to implement a sequencing of one or more ultra low magnetic fields substantially along one or more of the plurality of field directions; and a display 22 connected to the controller 20. Preferably, the controller 20 is further configured to reconstruct a displayable image of an electrical current density in the object 12. The preferred system 10 can function to provide simultaneous or substantially simultaneous imaging of an electrical current density within an object 12 through synchronous or substantially synchronous implementation of both electrical impedance tomography and magnetic resonance imaging (or functional magnetic resonance imaging.) The preferred system 10 can further function to provide substantial medical benefits by permitting real-time monitoring of a patient's neurological status allowing for accurate diagnosis and treatment planning for multiple disorders, including for example epilepsy, acute stroke, traumatic brain injury, and/or vasospasm. Furthermore, by accurately imaging the current flow through a patient's head tissues, the preferred system 10 can facilitate the development of advanced treatments for depression and rehabilitation from stroke or other neurological maladies through the direct application of current or of time-varying magnetic fields.

As shown in FIG. 1, the preferred system can include an electrical impedance tomography apparatus 14 electrically connectable to an object 12. Preferably, the electrical impedance tomography apparatus 14 can include a group of electrical leads and/or electrodes that are connectable to the object 12, such as for example a patient's head or other body part. Preferably, the electrical leads and/or electrodes can be distributed about an exterior of the object 12 such that there are numerous axes along which an electrical current can pass though the interior of the object 12. The impedance tomography apparatus 14 preferably functions to drive an electrical current of a predetermined direction, amplitude, frequency and phase through the object 12. In one example implementation, the electrical current can include a sinusoidal current with a frequency ranging between near direct current to approximately one megahertz. In operation, the electrical current preferably induces a voltage at some or all of the electrodes, from which amplitudes and phases can be determined by internal conductivity and permittivity distributions within the object 12. Preferably, boundary current/voltage data can be used by the controller 20 to reconstruct an image of the conductivity and/or permittivity distributions, thereby providing a representative image of at least a portion of the interior of the object 12.

Figures 2A, 2B, 2C:
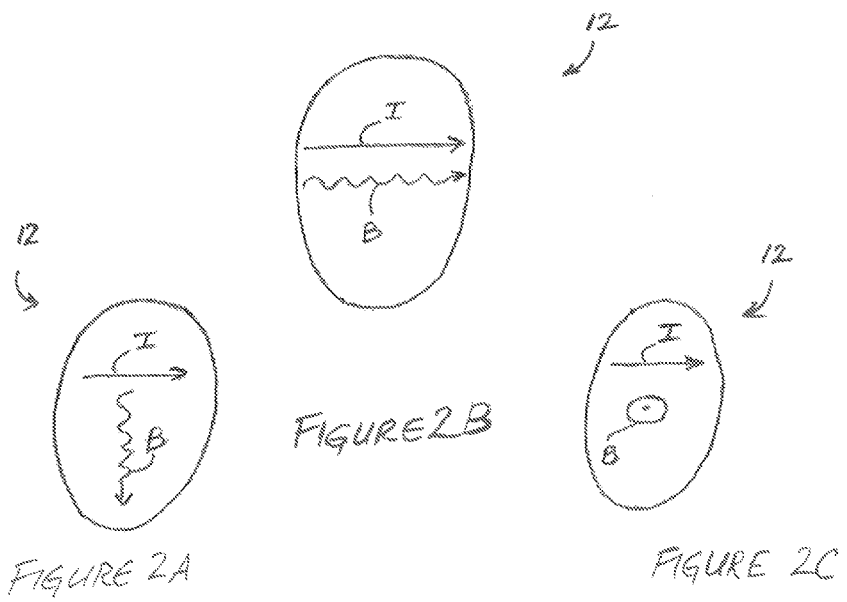
FIGS. 2A, 2B, and 2C are a schematic representation of several possible alignments of an electrical current and a magnetic resonance imaging magnetic field in accordance with variations of the preferred embodiment.

As shown in FIG. 1, the preferred system 10 can further include an ultra low field magnetic resonance imaging apparatus 16 including a plurality of field directions and disposable about the object 12. The ultra low field magnetic resonance imaging apparatus 16 preferably functions to image an interior of the object 12 in accordance with the general principles of magnetic resonance imaging. Preferably, low or ultra low magnetic fields (measurement fields) have amplitudes of less than 500, 250, 100, or 50 µT. Pre-polarization fields have amplitudes of less than about 500 mT, and typically on the order of 100-200 mT. For convenient illustration, cooling systems needed for SQUID operation are not shown in the Figures. As shown in FIG. 1, the ultra low field magnetic resonance imaging apparatus 16 can include one or more field generators 18a, 18b, 18c that are disposable about the object 12 in any suitable configuration. As shown in FIG. 1, the field generators 18a, 18b, 18c can be aligned along nominal Cartesian axes resulting in mutually orthogonal ultra low magnetic fields as shown in FIGS. 2A, 2B, and 2C. Alternatively, the field generators 18a, 18b, 18c can be arranged in any other suitable geometry, which can be fixed or variable depending upon the size and shape of the object 12 as well as the available current directions deliverable by the electrical impedance tomography apparatus 14.

As shown in FIG. 1, the preferred system can further include a controller 20 connected to the ultra low field magnetic resonance imaging apparatus 16 and configured to implement a sequencing of one or more ultra low magnetic fields substantially along one or more of the plurality of field directions. Selection, causation, sequencing, receipt, and interpretation of the various magnetic field signals is preferably determined by the controller 20, which can include a sequence library (not shown) that stores a variety of suitable pulse sequences. Resonant pulses have a sinusoidal or other time-varying waveform, with frequency proportional to the applied magnetic field strength (for protons, using 42.6 MHz/Tesla). Thus depending on field strength, which might be as low as a few µT, these pulses may not be at radio-frequencies. However, these pulses are referred to herein as RF pulses to indicate their traditional function. The actual frequencies depend on the applied magnetic field and nuclear species involved. Preferably, the controller 20 is configured to process detected magnetic resonance signals to produce specimen images, or partial images. Axial magnetic field coils (not shown) are situated to provide a suitable magnetic field (for example, a pre-polarization field) so as to establish a spin polarization in the object 12. The preferred system 10 can include additional coils for application of frequency encoding, phase encoding, slice selection, and spin flip pulses, including gradient pulses, but such coils are omitted from FIG. 1 for the purpose of clarity.

As shown in FIG. 1, the preferred system 10 can further include a display 22 coupled to the controller 20. The display 22 preferably functions to render, provide, project, image, and/or display a reconstructed depiction of the structure and/or function of the interior of the object 12 in response to the electrical current density within the object 12, the magnetic resonance properties of the object 12, and/or the interaction or resonance between the current density and the detected magnetic resonance. The display 22 can include any suitable apparatus or system, and can be integrated with or discretely connected to the controller 20 and/or any other components of the preferred system 10 or variations thereof. Those of skill in the art will further appreciate that the display 22 can be coupled to a user interface, such as for example a keypad, touchscreen, mouse, touchpad, and/or any other device for tactile, gesture, or voice command of the preferred system 10 or variations thereof.

As shown in FIGS. 2A, 2B, and 2C, in one variation of the preferred system 10, the electrical current I can generate an induced magnetic field (not shown) that is substantially parallel to at least one of the plurality of field directions B. As previously noted, FIG. 2 illustrates three distinct orientations of the ultra low magnetic field (i.e., measurement field) along a set of mutually orthogonal Cartesian axes. However, the ultra low field magnetic resonance imaging apparatus 16 can be oriented in any suitable manner, along any suitable axis or combination of axes, and around or about any desired object 12. Alternatively, the ultra low field magnetic resonance imaging apparatus 16 can include two or more coils (e.g., 18a, 18b, 18c) that can be selectively engaged to provide the ultra low magnetic field along the pertinent direction. In a typical example implementation, the at least one ultra low magnetic field will be aligned with respect to an induced magnetic field induced by the current driven by the impedance tomography apparatus 14. In another variation of the preferred system 10, any one of the at least one ultra low magnetic fields can be adjusted, sequenced, initiated, rotated, and/or reoriented between at least first and second states in which the orientation of the field relative to the induced field can be altered and/or adjusted. For example, a preferred sequencing of the one or more ultra low magnetic fields can include a first setting in which the ultra low magnetic field is substantially parallel to the induced magnetic field and a second setting in which the ultra low magnetic field is substantially obtuse (i.e., at an angle not including parallel or anti-parallel) to the induced magnetic field.

Figure 3:
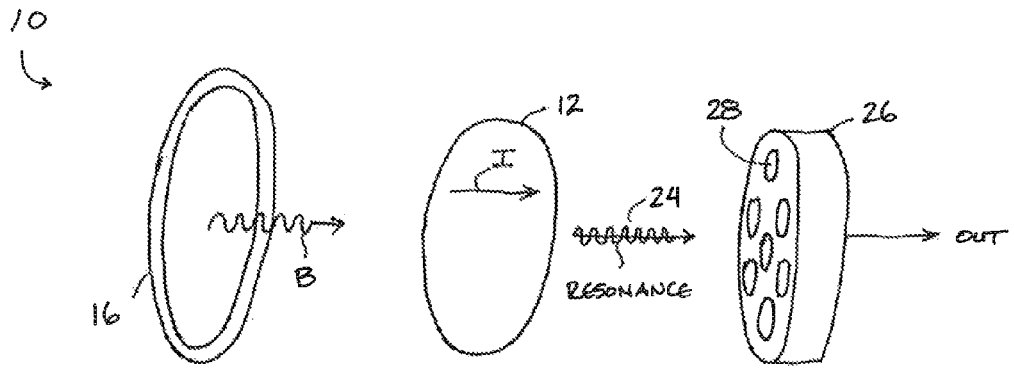
FIG. 3 is a schematic block diagram of an exemplary combination of ultra low magnetic field resonance imaging and electrical impedance tomography in accordance with another preferred embodiment of the present invention.
Figure 4:
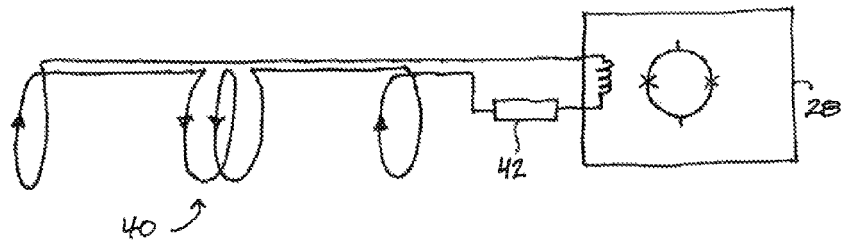
FIG. 4 is a schematic block diagram of an exemplary superconducting quantum interference device usable in one or more variations of the preferred embodiment of the present invention.

As shown in FIG. 3, in another variation of the preferred system 10, the ultra low field magnetic resonance imaging apparatus 16 can include a detector array 26 including one or more superconducting quantum interference devices (SQUIDs) 28 arranged in a predetermined geometry. The detector array 26 preferably functions to record, receive, interpret, input, and/or detect a resonance 24 achieved between the measurement field B and an induced magnetic field generated by the electrical current I. Alternatively, the preferred detector array 26 can be configured to record, receive, interpret, input and/or detect a phase shift produced by the magnetic field in the object B. In another alternative to the preferred system 10, the SQUIDS are switchable so as to reduce SQUID sensitivity during application of the pre-polarization magnetic field and at least portions of the measurement magnetic field and an imaging pulse sequence. FIG. 4 illustrates a schematic SQUID gradiometer that includes a gradient coil assembly 40 that is coupled to a SQUID 28 with a switch 42 that is configured to become resistive when heated. The switch 42 preferably has a switching time of about 5 μs and can be switched to have an increased resistance to reduce transients applied to the SQUID 28 as magnetic fields are applied or varied by the controller 20. Preferably, the SQUIDs 28 are enclosed within magnetic shields.

Figure 5:
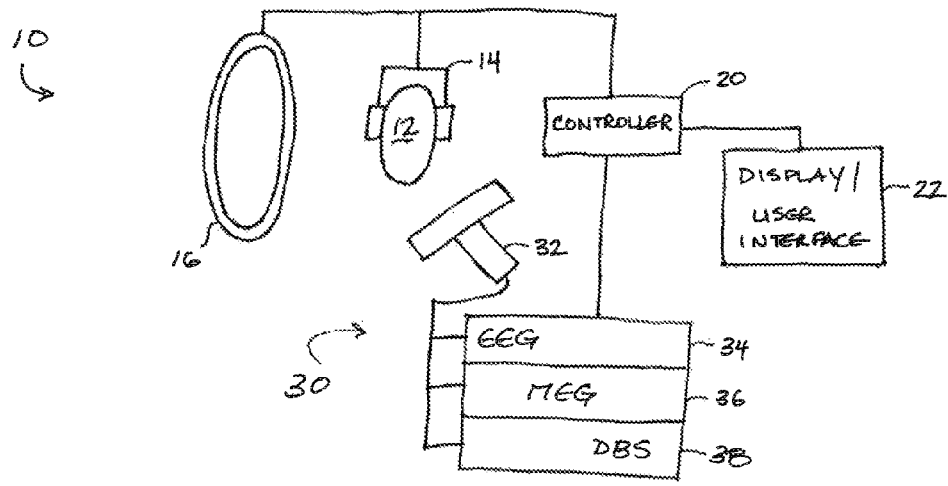
FIG. 5 is a schematic block diagram of an alternate system in which a preferred ultra low magnetic field resonance imaging system is combined with one or more other imaging and/or diagnostic systems/modalities.

As shown in FIG. 5, additional variations of the preferred system 10 can include additional and/or alternative imaging and/or treatment modalities 30 that can be performed simultaneously or substantially simultaneously with the magnetic resonance imaging 16 and/or the electrical impedance tomography 14. Preferably, the additional and/or alternative imaging and/or treatment modalities 30 can include an electroencephalography (EEG) apparatus 34 configured to record electrical activity along at least a portion of the head 12; a magneto-encephalography (MEG) apparatus 36 configured to record magnetic field activity within at least a portion of the head 12; and/or a transcranial brain stimulating apparatus 38 configured to transmit an electrical pulse to at least a portion of the head 12. Those of skill in the art will readily appreciate that each of the foregoing modalities 30 can include a specific interface, control, and/or detector/transmitter/receiver module 32 that is connected to and/or coupled with the object 12 for detection and/or processing of the appropriate signal/s. For example, an EEG apparatus 34 can include one or more electrodes; an MEG apparatus 36 can include one or more magnetic field detectors (such as one or more SQUIDS 28); and a transcranial brain stimulating apparatus 38 can include one or more stimulators, probes, wires, and/or tissue interfaces as appropriate.

Preferred Method

Figure 6:
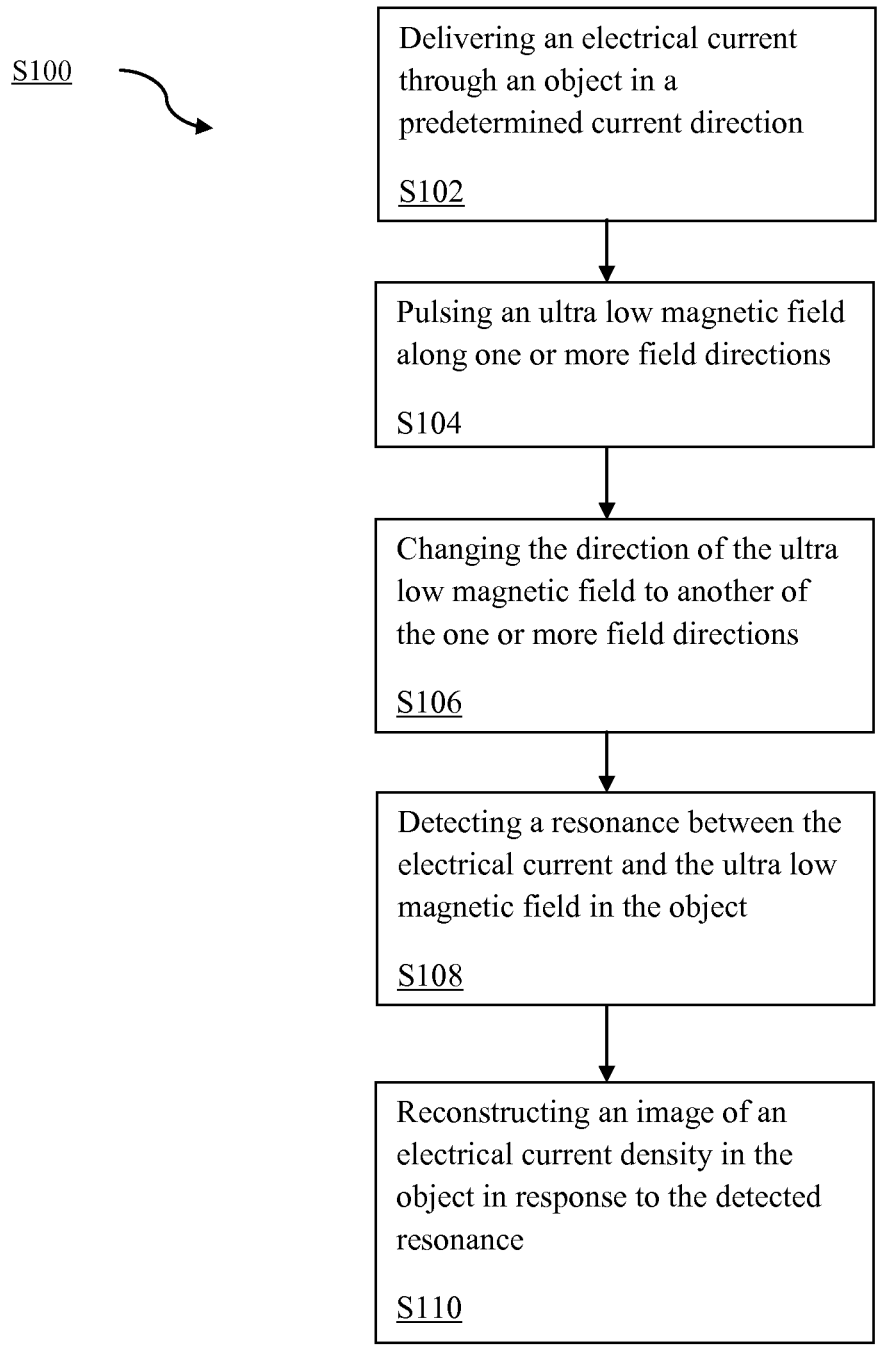
FIG. 6 is a flowchart depicting a method for magnetic resonance imaging at ultra low magnetic fields in accordance with a preferred embodiment.

As shown in FIG. 6, a method S100 according to a preferred embodiment can include delivering an electrical current through an object in a predetermined current direction in block S102; pulsing an ultra low magnetic field along one or more field directions in block S104; changing the direction of the ultra low magnetic field to another of the one or more field directions in block S106; detecting a resonance between the electrical current and the ultra low magnetic field in the object in block S108; and reconstructing an image of an electrical current density in the object in response to the detected resonance in block S110. The preferred method S100 functions to provide simultaneous or substantially simultaneous imaging of an electrical current density within an object through synchronous or substantially synchronous implementation of both electrical impedance tomography and magnetic resonance imaging (or functional magnetic resonance imaging.) As noted above, the preferred method S100 can further function to provide substantial medical benefits by permitting real-time monitoring of a patient's neurological status allowing for accurate diagnosis and treatment planning for multiple disorders, including for example epilepsy, acute stroke, traumatic brain injury, vasospasm, depression or other neurological maladies.

As shown in FIG. 6, the preferred method can include block S102, which recites an electrical current through an object in a predetermined current direction. Block S102 preferably functions to drive an electrical current of a predetermined direction, amplitude, and phase through the object, which is preferably a patient's head or other body portion of interest. Preferably, the electrical current can include a sinusoidal current with a frequency ranging between near direct current to approximately one megahertz. In operation, the electrical current preferably induces a voltage at one or more electrodes of an electrical impedance tomography device of the type described above, from which amplitudes and phases can be determined by internal conductivity and permittivity distributions within the object. As noted above, boundary current/voltage data can preferably be use reconstruct an image of the conductivity and/or permittivity distributions, thereby providing a representative image of at least a portion of the interior of the object 12.

As shown in FIG. 6, the preferred method S100 can further include block S104, which recites pulsing an ultra low magnetic field along one or more field directions. Block S104 preferably functions to image an interior of the object in accordance with the general principles of magnetic resonance imaging. Preferably, low or ultra low magnetic fields (measurement fields) have amplitudes of less than 500, 250, 100, or 50 μT. Pre-polarization fields have amplitudes of less than about 500 mT, and typically on the order of 100-200 mT. Suitable field directions can include for example nominal Cartesian axes resulting in mutually orthogonal ultra low magnetic fields. Alternatively, the field directions can be formed any other suitable geometry, which can be fixed or variable depending upon the size and shape of the object as well as the available current directions deliverable by the electrical impedance tomography apparatus in block S102.

As shown in FIG. 6, the preferred method S100 can further include block S106, which recites changing the direction of the ultra low magnetic field to another of the one or more field directions. Block S106 preferably functions to alter, adjust, and/or vary a direction of the ultra low magnetic field in order to align the ultra low magnetic field with one or more induced magnetic fields in the object, such as for example the magnetic field induced by the current delivered in block S102. In one variation of the preferred method, block S106 can include selecting between two or more distinct ultra low magnetic field generators having distinct directionality. Alternatively, block S106 can include selectively rotating, adjusting, moving, and/or changing a position of a single ultra low magnetic field generator with respect to the object. Such a relative change in position can be accomplished by moving one or both of the ultra low magnetic field generator/s or the object. For example, a preferred sequencing of the one or more ultra low magnetic fields can include a first setting in which the ultra low magnetic field is substantially parallel to the induced magnetic field and a second setting in which the ultra low magnetic field is substantially obtuse (i.e., at an angle not including parallel or anti-parallel) to the induced magnetic field.

As shown in FIG. 6, the preferred method 5100 can further include block 5108, which recites detecting a resonance between the electrical current and the ultra low magnetic field in the object. Block 5108 preferably functions to record, receive, interpret, input, and/or detect a resonance achieved between the ultra low magnetic field (a measurement field B) and an induced magnetic field generated by the electrical current I. Block S108 can additionally or alternatively record, receive, interpret, input and/or detect a phase shift produced by the magnetic field in the object. Preferably, block 5108 can be performed by an array of SQUIDS of the type described above. One variation of the preferred method can include switching one or more SQUIDS so as to reduce SQUID sensitivity during application of the pre-polarization magnetic field and at least portions of the measurement magnetic field and an imaging pulse sequence.

As shown in FIG. 6, the preferred method can further include block 5110, which recites reconstructing an image of an electrical current density in the object in response to the detected resonance. Block S110 preferably functions to render, provide, project, image, and/or display a reconstructed depiction of the structure and/or function of the interior of the object in response to the electrical current density within the object, the magnetic resonance properties of the object, and/or the interaction or resonance between the current density and the detected magnetic resonance. Block S110 can additionally or alternatively include reconstructing an image of an electrical current density in the object in response to a detected phase shift produced by the magnetic field in the object. Block 5110 is preferably performed by a controller and/or display of the type described above.

As noted above, additional variations of the preferred method 5100 can further include any or all of performing an EEG on the head; performing a magneto-encephalogram on the head; and/or performing transcranial brain stimulation in the head. Each of the aforementioned additional and/or alternative imaging and/or treatment modalities can be performed simultaneously, substantially simultaneously, or in lieu of the magnetic resonance imaging and/or the electrical impedance tomography.

Figure 7:
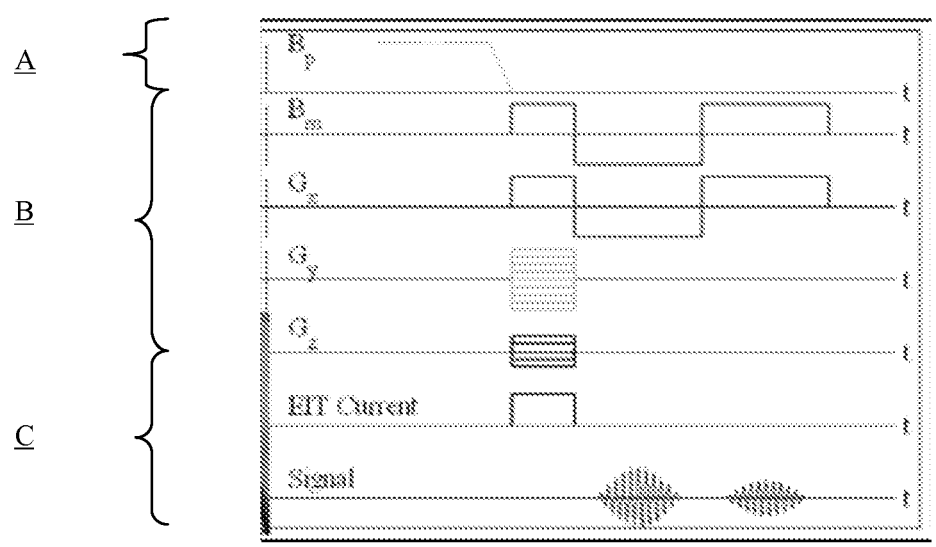
FIG. 7 is a schematic diagram of an example sequencing of ultra low field magnetic resonance imaging in combination with electrical impedance tomography in accordance with one variation of the preferred system and method.

FIG. 7 illustrates a representative pulse sequence associated with combined magnetic resonance imaging and electrical impedance tomography procedures. A pre-polarization magnetic field $B_p$ having a magnitude of about a few hundred mT is applied at (A), and a series of ultra low magnetic field pulses are applied or magnetic resonance imaging signals received at (B). The field $B_p$ is preferably turned off or reduced, and a measurement field $B_m$ of magnitude of a few hundred µT is applied. Detected magnetic resonance imaging signals are based on spin precession associated with $B_m$, and the much larger pre-polarization field is not present during transmission of the electrical impedance tomography signal or detection of the magnetic resonance with the induced magnetic field at (C).

An alternative embodiment preferably implements the one or more aspects of the preferred system and/or methods in a computer-readable medium storing computer-readable instructions. The instructions are preferably executed by computer-executable components, such as those found in one or more of the controller 20, the display 22, and/or the detector 26. The computer-readable medium can be stored on any suitable computer readable media such as RAMs, ROMs, flash memory, EEPROMs, optical devices (CD or DVD), hard drives, floppy drives, or any suitable device. The computer-executable component is preferably a processor but the instructions may alternatively, or additionally, be executed by any suitable dedicated hardware device. The computer-executable component is preferably designed for any suitable computing platform.

The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation. Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

As a person skilled in the art will recognize from the previous detailed description and from the figures and claims, modifications and changes can be made to the preferred embodiments of the invention without departing from the scope of this invention defined in the following claims.

What is claimed is:

1. An imaging system comprising:
    an electrical impedance tomography apparatus comprising one or more electrical leads adapted to deliver an electrical current through an object in a predetermined current direction;
    an ultra low field magnetic resonance imaging apparatus comprising a plurality of field directions and disposable about the object and configured to emit one or more ultra low magnetic field pulses comprising one or more measurement magnetic fields ranging between one and three hundred microtesla in amplitude wherein an induced magnetic field generated b the electrical current is substantially parallel to at least one of the plurality of field directions;
    a controller connected to the ultra low field magnetic resonance imaging apparatus and configured to implement a sequencing of the one or more ultra low magnetic field pulses substantially along one or more of the plurality of field directions, wherein the sequencing of the one or more ultra low magnetic field pulses comprises a first setting in which the ultra low magnetic field pulse is substantially parallel to the induced magnetic field and a second setting in which the ultra low magnetic field pulse is substantially perpendicular to the induced magnetic field; and a display connected to the controller, and wherein the controller is further configured to reconstruct a displayable image of an electrical current density in the object.

2. The system of claim 1, wherein the ultra low field magnetic resonance imaging apparatus comprises a detector array comprising one or more superconducting quantum interference devices arranged in a predetermined geometry.

3. The system of claim 1, wherein the one or more measurement magnetic fields are less than one hundred microtesla in amplitude.

4. The system of claim 1, wherein the object comprises a head and further comprising an electroencephalography apparatus configured to record electrical activity along at least a portion of the head.

5. The system of claim 1, wherein the object comprises a head and further comprising a magneto-encephalography apparatus configured to record magnetic field activity within at least a portion of the head.

6. The system of claim 1, wherein the object comprises a head and further comprising a transcranial brain stimulating apparatus configured to transmit an electrical pulse to at least a portion of the head.

7. A method comprising:
   delivering an electrical current through an object in a predetermined current direction;
   pulsing an ultra low magnetic field substantially parallel to the induced magnetic field wherein the ultra low magnetic field com rises a measurement magnetic field ranging between one and three hundred microtesla in amplitude;
   changing the direction of the ultra low magnetic field by pulsing the ultra low magnetic field substantially perpendicular to the induced magnetic field wherein an induced magnetic field generated by the electrical current is substantially parallel to at least one of one or more field directions;
   detecting a resonance between the electrical current and the ultra low magnetic field in the object; and
   reconstructing an image of an electrical current density in the object in response to the detected resonance.

8. The method of claim 7, wherein the measurement magnetic field is less than one hundred microtesla in amplitude.

9. The method of claim 7, wherein the object comprises a head and further comprising performing an electroencephalogram on the head.

10. The method of claim 7, wherein the object comprises a head and further comprising performing a magnetoencephalogram on the head.

11. The method of claim 7, wherein the object comprises a head and further comprising performing transcranial brain stimulation in the head.

12. A computer program product comprising a non-transitory computer readable medium comprising computer executable code embodied therein, the computer executable code comprising a set of instructions to cause a computer to:
   deliver an electrical current through an object in a predetermined current direction;
   pulse an ultra low magnetic field substantially parallel to the induced magnetic field, wherein the ultra low magnetic field com rises a measurement magnetic field ranging between one and three hundred microtesla in amplitude;
   change the direction of the ultra low magnetic field by pulsing the ultra low magnetic field substantially perpendicular to the induced magnetic, field wherein an induced magnetic field generated by the electrical current is substantially parallel to at least one of one or more field directions;
   detect a resonance between the electrical current and the ultra low magnetic field in the object; and
   reconstruct an image of an electrical current density in the object in response to the detected resonance.

13. The computer program product of claim 12, wherein the measurement magnetic field is less than one hundred microtesla in amplitude.

* * * * *